(12) United States Patent
Tanzer

(10) Patent No.: US 6,290,686 B1
(45) Date of Patent: Sep. 18, 2001

(54) ABSORBENT ARTICLE HAVING IMBRICATED SUPERABSORBENT TILES ON A SUBSTRATE

(75) Inventor: Richard Warren Tanzer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/384,976

(22) Filed: Aug. 27, 1999

(51) Int. Cl.[7] .............................. A61F 13/15; A61F 13/20
(52) U.S. Cl. .................... 604/385.01; 604/358; 604/359; 604/367; 604/385.23
(58) Field of Search ............................... 604/385.01, 378, 604/359, 385.23, 385.101, 358, 367

(56) References Cited

U.S. PATENT DOCUMENTS

| | | | |
|---|---|---|---|
| 5,364,382 | 11/1994 | Latimer et al. | 604/378 |
| 5,509,915 | 4/1996 | Hanson et al. | 604/378 |
| 5,863,288 * | 1/1999 | Baker | 604/378 |
| 5,968,029 * | 10/1999 | Chappell et al. | 604/385.1 |
| 5,977,003 * | 11/1999 | Wilshaw et al. | 501/80 |
| 6,160,198 * | 12/2000 | Roe et al. | 604/361 |
| 6,171,290 * | 1/2001 | Boisse et al. | 604/385.01 |

* cited by examiner

Primary Examiner—John G. Weiss
Assistant Examiner—Michele Kidwell
(74) Attorney, Agent, or Firm—Pauley Petersen Kinne & Fejer

(57) ABSTRACT

An absorbent article is provided with an absorbent composite including a plurality of discrete superabsorbent-containing entities arranged on a substrate. The superabsorbent-containing entities are imbricated, meaning that the leading edge of each entity overlaps the trailing edge of each successive entity. When the absorbent article becomes wet and the superabsorbent expands, the adjacent entities slide over each other and the degree of overlap is increased. Accordingly, the expansion of the superabsorbent article causes the "Z" directional thickness of the absorbent composite to increase, and the effect of the expansion on the longitudinal and lateral ("X" and "Y") dimensions is minimized.

20 Claims, 2 Drawing Sheets

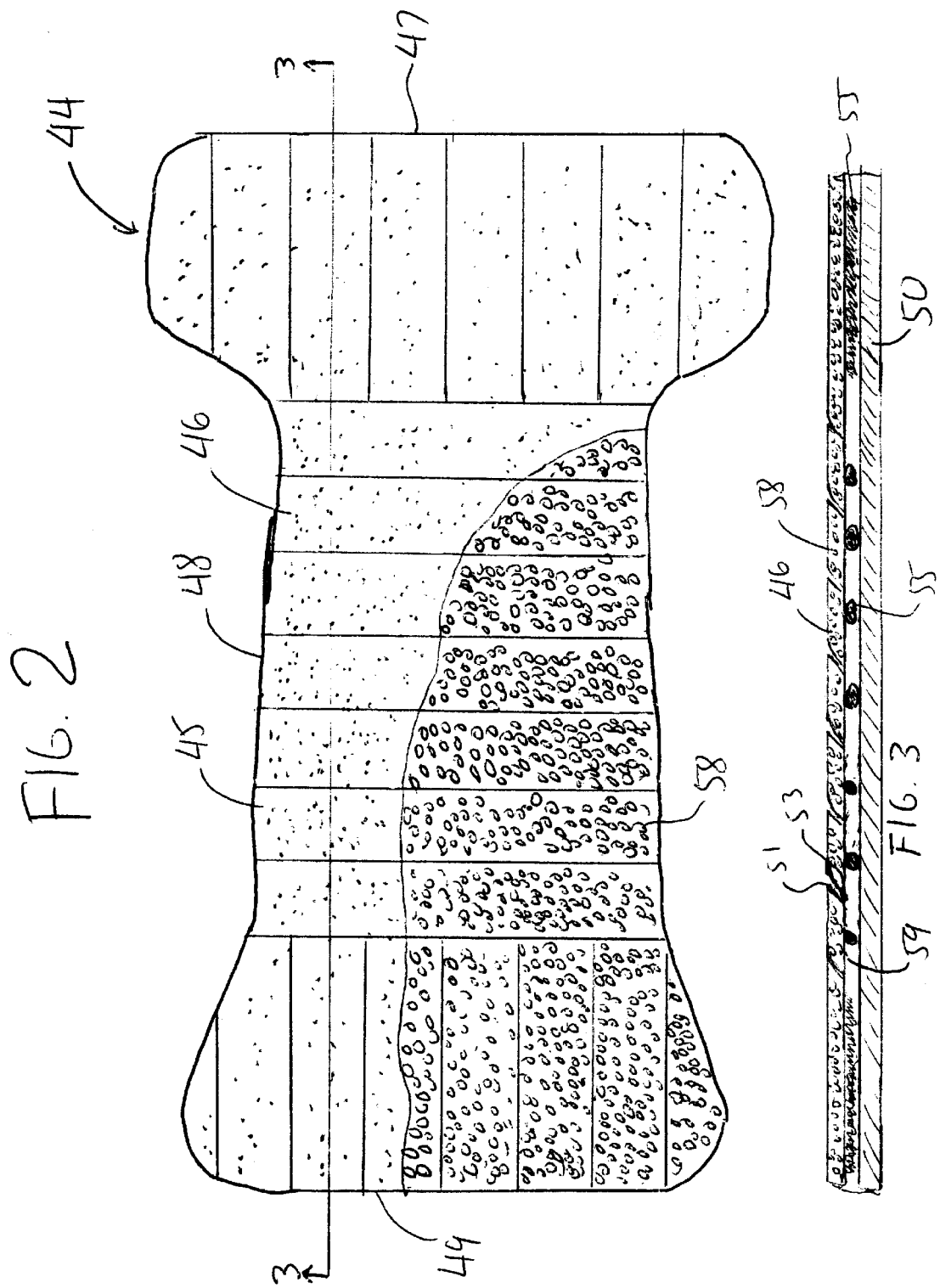

ABSORBENT ARTICLE HAVING IMBRICATED SUPERABSORBENT TILES ON A SUBSTRATE

FIELD OF THE INVENTION

This invention is directed to an absorbent article in which discrete superabsorbent entities are attached to a substrate. The superabsorbent entities have edges which overlap each other when the substrate is in a relaxed, non-extended position, and when the absorbent article is dry.

BACKGROUND OF THE INVENTION

Absorbent composites having a superabsorbent material contained in discrete pockets in a substrate are disclosed in U.S. Pat. No. 5,601,542, issued Feb. 11, 1997 to Melius et al. A plurality of pockets having spaces between them are formed in a substrate which can be a cloth-like woven or nonwoven web, a closed or open-celled foam, a perforated film, an elastic material, or a fibrous web. A superabsorbent material is loaded into the pockets. When the composite becomes wet, the superabsorbent expands, and the adjacent pockets are urged toward each other.

This expansion of pockets may cause the entire absorbent composite to expand, in a lateral and/or longitudinal direction. Thus, the dimensions of the absorbent composite (and, often, the entire absorbent article) may increase laterally and/or longitudinally when the article becomes wet. An absorbent article which fits snugly or tightly when dry, may fit loosely and not as well when wet. There is a need or desire for an absorbent article containing discrete superabsorbent entities, whose lateral and longitudinal dimensions do not significantly change when the article becomes wet.

SUMMARY OF THE INVENTION

The present invention is directed to an absorbent article having discrete superabsorbent entities attached to a substrate layer. The superabsorbent entities are imbricated, meaning that the adjacent superabsorbent entities have overlapping edges when the absorbent article is dry. When the absorbent article becomes wet and the superabsorbent expands, the amount of overlap between adjacent superabsorbent entities increases. The net effect is that the expansion of superabsorbent increases the thickness of the superabsorbent composite without significantly increasing the lateral and longitudinal dimensions of the absorbent composite.

The discrete superabsorbent entities may be in the form of rectangular tiles, circular or semi-circular plates or saucers, elliptical or ovular pillows, or any other shape which permits the edges of adjacent entities to overlap each other while being attached to the same substrate. Each superabsorbent entity may include a quantity of superabsorbent particles or fibers contained in a liquid-permeable cover or "pillowcase" which maintains the discreteness of the entities, i.e., which allows aqueous liquid to pass through but does not permit passage of the contained superabsorbent particles or fibers. The cover sheet may be a fibrous woven or nonwoven web, an apertured film, or open-celled foam material, a mesh plastic screen or net, or a combination including one or more of these.

The substrate may be a stretchable or non-stretchable layer material, and may be a film, a woven or nonwoven web, a foam layer, or a combination including one or more of these. Each discrete superabsorbent entity is affixed to the substrate along a point or line which leaves most of the entity free of binding from the substrate, and able to lift off of the substrate to facilitate the imbrication of adjacent entities.

With the foregoing in mind, it is a feature and advantage of the invention to provide an absorbent composite having discrete superabsorbent entities attached to a substrate, which expands more in thickness (the "Z" direction) when wet than in the lateral or longitudinal ("X" or "Y") directions.

It is also a feature and advantage of the invention to provide an absorbent article having consistent fit whether wet or dry, and having more expansion in the "Z" direction when wet, than in the "X" or "Y" directions.

The foregoing and other features and advantages will become further apparent from the following detailed description of the presently preferred embodiments, read in conjunction with the drawings.

BRIEF DESCRIPTION OF THE DRAWINGS

FIG. 2 is a partially cut away plan view of an absorbent composite useful in the diaper of FIG. 1.

FIG. 3 is a sectional view taken along line 3—3 in FIG. 2.

DETAILED DESCRIPTION OF THE PRESENTLY PREFERRED EMBODIMENTS

Figure 1:
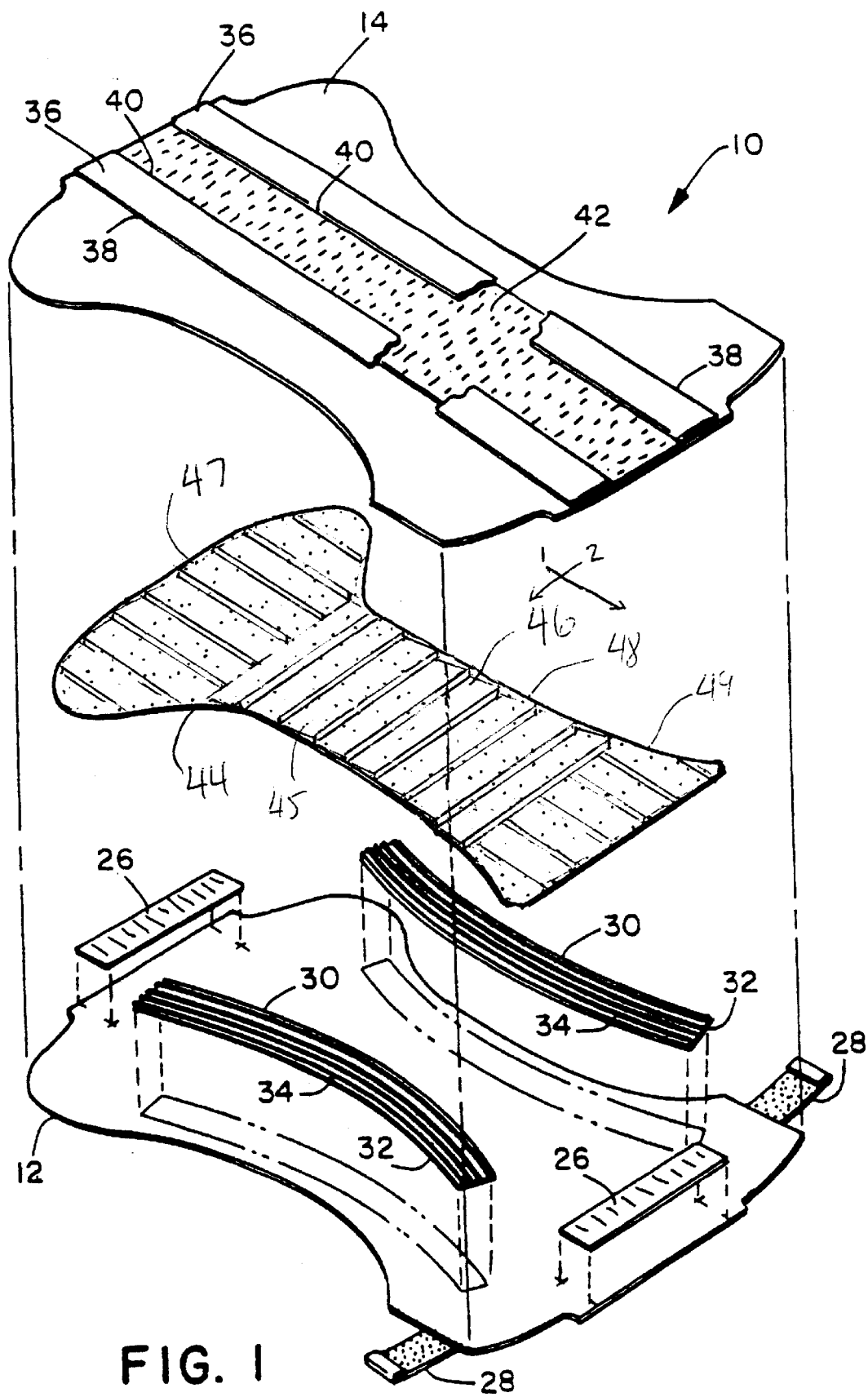
FIG. 1 is an exploded perspective view of an absorbent article of the invention, in this case a diaper.

The present invention is an absorbent article having imbricated discrete superabsorbent entities attached to a substrate. The term "absorbent article" includes without limitation diapers, training pants, swim wear, absorbent underpants, adult incontinence products, feminine hygiene products and medical absorbent products (for example, absorbent medical garments, underpads, bandages, drapes, and medical wipes).

The term "imbricated discrete superabsorbent-containing entities" refers to superabsorbent contained in rectangular tiles, curved platelets, saucers, or other similar entities having edges. The entities are placed so that an edge of one of the entities overlaps an edge of another adjacent one of the entities when the entities containing the superabsorbent are dry. When the entities become wet, the amount of overlap between adjacent superabsorbent entities may become greater due to expansion of the superabsorbent. For a given entity, the superabsorbent is generally wrapped or otherwise contained in a liquid-permeable layer material which allows liquid to readily enter the entity, but prevents superabsorbent particles or fibers from leaving the entity. The layer material may be an apertured or otherwise porous film, a fibrous woven or nonwoven web, an open-celled foam material, or another suitable material.

The term "substrate" refers to any layer material or combination of layers, whether stretchable or not, including without limitation polymeric films, nonwoven webs, open-celled foams, and the like. The term "stretchable" means that a material can be stretched, without breaking, to at least 150% of its initial (unstretched) length in at least one direction, suitably to at least 200% of its initial length, desirably to at least 250% of its initial length. "Elastic" materials are stretchable materials that tend to recover or retract most of the way to their initial length when the stretching force is removed. An elastic material should recover at least 50% of the way to its initial length when a stretching force is removed, preferably at least 75% of the way to its initial length. The term "not stretchable" means that a material can only be stretched to less than 150% of its initial length in all directions, suitably to less than 130% of its initial length, desirably to less than 110% of its initial length.

One preferred absorbent article is a disposable diaper. FIG. 1 illustrates an exploded perspective view of a disposable diaper according to one embodiment of the present invention. Disposable diaper 10 includes an outer cover 12, a body-side liner 14, and an absorbent composite 44 located between the body-side liner 14 and the outer cover 12. The absorbent composite 44 comprises a plurality of imbricated absorbent tiles 46 containing a superabsorbent material and, optionally, wood pulp fibers or another material as further described below. The tiles 46 are rectangular in shape. Each tile 46 represents a discrete superabsorbent entity and includes a liquid pervious cover sheet 45 which allows liquid to enter the tiles but prevents superabsorbent material from migrating between tiles. Each tile 46 has a leading edge which overlaps a trailing edge of the next adjacent tile. In the embodiment shown in FIG. 1, tiles 46 in a central region 48 are oriented in a longitudinal direction shown by an arrow 1. Tiles 46 in end regions 47 and 49 (corresponding to waist regions on a wearer) are oriented in a lateral direction indicated by arrow 2. These orientations of tiles 46 correspond to preferred directions of stretch of diaper 10 during wear, in the central and end regions.

Attached to outer cover 12 are waist elastics 26, fastening tapes 28 and leg elastics 30. The leg elastics 30 comprise a carrier sheet 32 and individual elastic strands 34.

The body-side liner 14 includes containment flaps 36 having proximal edges 38 and distal edges 40. A surge management layer 42 is located between the proximal edges 38 of the containment flaps 36.

A possible construction method and materials of a diaper similar to the one illustrated in FIG. 1 are set forth in greater detail in commonly assigned U.S. Pat. No. 5,509,915, issued Apr. 25, 1996 in the name of Hanson et al., incorporated herein by reference. Possible modifications to the diaper illustrated in FIG. 1 are set forth in commonly assigned U.S. Pat. No. 5,509,915 referenced above and in commonly assigned U.S. Pat. No. 5,364,382, issued Nov. 15, 1994 in the name of latimer et al. Such possible modifications include positioning the surge management layer 42 between the body-side liner 14 and the absorbent composite 44 and reducing the length of the surge management layer to extend the length of the absorbent composite or massing (reduce length and increase basis weight) the surge management layer in the area of the diaper where liquid waste initially accumulates (target zone).

FIGS. 2 and 3 illustrate the absorbent composite 44 in greater detail. A superabsorbent material 58, which can be particles or fibers, is contained by the cover sheet 45 within each of the tiles 46. The superabsorbent 58 within the discrete entities 46 may be alone or in combination with another material. Materials which can be blended with superabsorbent 58 include other absorbent materials, such as pulp fibers. Fillers, odor absorbents, fragrances, and other suitable materials may also be combined with superabsorbent 58. When combinations of materials are employed, the superabsorbent 58 should constitute at least 20% by weight of the total material contained in files 46, suitably at least 40% by weight, desirably at least 60% by weight and, in some instances, at least 80% by weight.

The term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride. The superabsorbent materials can be natural, synthetic, and modified natural polymers and materials. In addition, the superabsorbent materials can be inorganic materials, such as silica gel, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations of Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbents may be particulate or fibrous, and are preferably particulate. Superabsorbents are generally available in particle sizes ranging from about 20 to about 1000 microns. Examples of commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® 880 available from Stockhausen, located in Sweden. FAVOR® 880 is presently preferred because of its high gel strength. An example of a fibrous superabsorbent is OASIS® 101, available from Technical Absorbents, located in Grimsby, United Kingdom.

The cover material 45 may be any liquid pervious material having pores or other openings large enough to readily transmit liquid, yet small enough to substantially contain the superabsorbent material 58. Preferably, the cover material 45 should be sufficiently stretchable to accommodate expansion of the superabsorbent 58 due to wetness. Suitable materials include porous woven materials, porous nonwoven materials (e.g., spunbond and meltblown webs), and apertured films. Examples include, without limitation, any stretchable porous sheet of polymeric fibers, bonded carded webs of synthetic or natural fibers, or combinations thereof. The cover material 45 may also be an apertured stretchable plastic film. The cover material 45 should be sufficiently thick to contain the superabsorbent 58 during expansion. Cover material 45 may have a basis weight of about 0.2–8 ounces per square yard (osy) (about 6.8–270 grams/m$^2$, or gsm), suitably about 0.4–4 osy (13.6–135 gsm).

A wide variety of polymers maybe used to make the cover material 45 including without limitation, polyolefins (including polyethylene, polypropylene, and alpha-olefin copolymers thereof; diblock, triblock or multi-block elastomeric copolymers such as olefinic copolymers, including styrene-isoprene-styrene, styrene-butadiene-styrene, styrene-ethylene/butylene-styrene, or styrene-ethylene/ propylene-styrene, which may be obtained from the Shell Chemical Company, under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having density less than about 0.89 grams/cc, available from Dow Chemical Co. under the trade name AFFINITY®.

Alternatively, the discrete absorbent entities 46 may be comprised of a matrix material which effectively retains superabsorbent 58 even without a cover material 45. Examples of composite materials which inherently retain superabsorbent include coformed meltblown microfibers with superabsorbent and, optionally, wood pulp or cotton linters. In a coform process, at least one meltblown die head is arranged near a chute, through which other materials are added while the web is forming. Coform processes are described in U.S. Pat. Nos. 4,818,464 to Lau and 4,100,324 to Anderson et al., the disclosures of which are incorporated by reference. Other composites and materials which inherently retain superabsorbent include open celled foams with entrapped superabsorbent particles; knitted, woven and nonwoven mats of superabsorbent fibers; and superabsorbent films.

The amount of superabsorbent 58 in each discrete entity 46 may vary depending on the size of entities 46, the concentration of superabsorbent and other materials, and the absorbent properties required for the end use application. Entities or tiles 46 may each contain about 0.1–15 grams of superabsorbent, suitably about 0.2–10 grams of superabsorbent, desirably about 0.4–4 grams of superabsorbent. It is desirable that the amount of superabsorbent in the entities 46, and the number of entities 46, be sufficient that the superabsorbent provides at least 70% of the absorbent capacity of the entire article, preferably at least 90%. Each entity 46 may, when dry, be about 0.5–2.5 cm thick, about 1–5 cm long, and about 1–5 cm wide.

The absorbent entities 46 may be sealed and attached to the substrate at a plurality of attachment lines or points 55 (FIG. 3). The sealing and attachment can be accomplished using a variety of known techniques including adhesive bonding (hot melt adhesives, glues, spray adhesives, solvent-based adhesives and the like), thermal bonding, ultrasonic bonding, stitch bonding and the like. One suitable stretchable hot melt adhesive is 2525A, available from Findlay Adhesives Co. As shown in FIG. 3, the attachments 55 should cover substantially less than the underside 59 of each tile 46, preferably covering less than 35%, more preferably less than 25% of the underside of each tile 46. This way, when the tiles 46 expand due to wetting of the superabsorbent, each leading edge 51 is able to expand and slide so as to further overlap the trailing edge 53 of an adjacent tile. As a result of this expansion via increased overlap, the wetting of the superabsorbent causes the absorbent composite 44 to assume greater thickness and bulk in a "Z" direction, and avoids much of the expansion in the "X" and "Y" (longitudinal and lateral) directions that would occur if the tiles did not overlap, but instead expanded against each other laterally and/or longitudinally.

The substrate 50 may be a woven or nonwoven fibrous web, a polymer film, a polymer foam, or any combination including one or more of these. Substrate 50 may include one or more layers, and may have a basis weight of about 0.2–10 osy (6.8–340 gsm), desirably about 0.5–5 osy (17–170 gsm), preferably 1–2 osy (34–68 gsm). Substrate 50 may be formed from any one or more of the polymers listed above for the cover material 45, or from a different polymer material.

In an alternative embodiment, substrate 50 may be folded or otherwise configured so that it also functions as a cover material 45. For example, a continuous section of substrate 50 may be folded over to yield pockets, and the pockets may be filled with superabsorbent and sealed. To accomplish this, the substrate 50 need only be folded so that it has a corrugated, accordion-like configuration. Each corrugation may serve as a separate pocket. However, the substrate 50 would need to be highly liquid-permeable in order to serve this function.

Preferably, the substrate 50 is both elastic and permeable to water vapor. The substrate 50 may be made from a water vapor permeable elastic polymer, or may be made from another elastic polymer and rendered vapor permeable by forming apertures or micropores in the sheet. Preferably, the substrate 50 has a moisture vapor transmission rate (MVTR) of at least about 500 grams/m$^2$-24 hours, more preferably at least about 1200 grams/m$^2$-24 hours, most preferably at least about 2000 grams/m$^2$-24 hours using the test procedure described below. The MVTR is a function of both film thickness and polymer type. Elastic polymers which exhibit the required MVTR over a range of useful film thicknesses include without limitation vulcanized silicone rubber, some other silicone polymers, polyurethanes, polyether esters and polyether amides. The following Table 1 gives representative water vapor permeabilities of exemplary elastic polymers, adjusted for film thickness of a pure polymeric film.

TABLE 1

| Polymer Type | Water Vapor Permeability, kg-cm/(km)$^2$-day |
| --- | --- |
| Vulcanized silicone rubber | 11,900 |
| Polyurethane-Estane ® 58237 | 760 |
| Polyurethane-Estane ® 58245 | 1,270 |
| Polyether amide-PEBAX ® | 830 |
| Polyether ester Hytrel ® or Arnitel ® | 930 |
| Polyester-polyurethane copolymer | 160 |
| Polyether-polyurethane copolymer | 310 |

If the elastic polymer has low water vapor permeability, the substrate 50 may have to be extremely thin in order to achieve the desired minimum level of MVTR. Elastomers having lower vapor permeability include, for instance, styrene-butadiene copolymers and terpolymers, elastomeric ethylene-propylene copolymers, ethylene-propylene-diene rubbers, and certain single-site or metallocene-catalyzed ethylene polymers and ethylene-alpha olefin copolymers having a density not exceeding 0.89 grams/cc. Alternatively, the elastic film may be thicker, and may be rendered porous or microporous using numerous techniques familiar to persons skilled in the art.

As explained above, the overlap of the tiles 46 can be oriented in a direction where the substrate 50 is likely to experience the most stretching. Thus, tiles 46 in the central region 48 of absorbent composite 44 may overlap in the longitudinal direction 1, because central region 48 (if composite 44 is in a diaper) is most likely to be stretched longitudinally. Tiles 46 in end regions 47 and 49 may overlap in the lateral direction 2, because end regions 47 and 49 are most likely to be stretched laterally. The bonding regions 55 (FIG. 3) may be in the form of bond lines which are parallel to the overlapping edges of the tiles. This way, when tiles 46 become wet, bond regions 55 do not inhibit or prevent adjacent tiles from expanding in a direction of increased overlap, causing the absorbent composite 44 to preferentially become thicker, as opposed to longer or wider.

Both the surge layer 42 and the body side liner 14 are constructed from highly liquid pervious materials. These layers function to transfer liquid from the wearer to the absorbent composite 44. Suitable materials include porous woven materials, porous nonwoven materials, and apertured films. Examples include, without limitation, any stretchable porous sheets of polymeric fibers, bonded carded webs of synthetic or natural fibers or combinations thereof. Either layer may also be an apertured stretchable plastic film.

The outer cover 12 may include a single stretchable layer, or may include multiple stretchable layers joined together by adhesive bonding, thermal bonding, ultrasonic bonding or the like. Outer cover 12 can be made from a wide variety of woven or nonwoven material, films, or a film-coated nonwoven material, including, for instance, cast or blown films. Outer cover 12 may also be a composite of a bonded carded or spunbonded or meltblown material, for example, a spunbonded-meltblown composite of thermoplastic material or a spunbonded-meltblown-spunbonded thermoplastic material, wherein the spunbonded layer can provide a cloth-like texture and the meltblown layer can provide liquid impermeability. Outer cover 12 is preferably highly breathable to water vapor.

Test Procedure For Measuring Moisture Vapor Transmission Rate (MVTR)

A measure of the breathability of a fabric is the moisture vapor transmission rate (MVTR), which for the sample materials is calculated essentially in accordance with ASTM Standard E96-80 with minor variations in test procedure as set forth below. Circular samples measuring three inches in diameter are cut from each of the test materials, and tested along with a control which is a piece of CELGARD® 2500 sheet from Celanese Separation Products of Charlotte, N.C. CELGARD® 2500 sheet is a microporous polypropylene sheet. Three samples are prepared for each material. The test dish is a number 60-1 Vapometer pan distributed by Thwing-Albert Instrument Company of Philadelphia, Pa. One hundred milliliters of water is poured into each Vapometer pan and individual samples of the test materials and control material are placed across the open tops of the individual pans. Screw-on flanges are tightened to form a seal along the edges of the pan, leaving the associated test material or control material exposed to the ambient atmosphere over a 6.5 centimeter diameter circle having an exposed area of approximately 33.17 square centimeters. The pans are placed in a forced air oven at 100° F. (32° C.) for 1 hour to equilibrate. The oven is a constant temperature oven with external air circulating through it to prevent water vapor accumulation inside. A suitable forced air oven is, for example, a Blue M Power-O-Matic 60 oven distributed by Blue M Electric Company of Blue Island, Ill. Upon completion of the equilibration, the pans are removed from the oven, weighed and immediately returned to the oven. After 24 hours, the pans are removed from the oven and weighed again. The preliminary test water vapor transmission rate values are calculated as follows:

$$\text{Test MVTR} = (\text{grams weight loss over 24 hours}) \times 315.5 \text{ g/m}^2\text{-24 hours}$$

The relative humidity within the oven is not specifically controlled.

Under predetermined set conditions of 100° F. (32° C.) and ambient relative humidity, the MVTR for the CELGARD® 2500 control has been defined to be 5000 grams per square meter for 24 hours. Accordingly, the control sample is run with each test and the preliminary test values are corrected to set conditions using the following equation:

$$\text{MVTR} = (\text{Test MVTR/control MVTR}) \times (5000 \text{ g/m}^2\text{-24 hours})$$

While the embodiments disclosed herein are presently considered preferred, various modifications and improvements can be made without departing from the spirit and scope of the invention. The scope of the invention is indicated by the appended claims, and all changes that fall within the meaning and range of equivalency are intended to be embraced therein.

I claim:

1. An absorbent composite, comprising:
   a substrate layer material; and
   a plurality of discrete superabsorbent-containing entities attached to the substrate, each discrete superabsorbent-containing entity being attached only to the substrate at an attachment point which leaves most of the entity free of binding so that adjacent entities may expand and slide relative to each other;
   the superabsorbent-containing entities being imbricated so that a leading edge of at least some of the superabsorbent-containing entities overlaps a trailing edge of an adjacent superabsorbent-containing entity.

2. The absorbent article of claim 1, wherein the plurality of discrete superabsorbent-containing entities further contain an odor absorbent.

3. The absorbent article of claim 1, wherein the plurality of discrete superabsorbent-containing entities further contain a fragrance.

4. The absorbent article of claim 1, wherein the substrate layer material comprises a plastic foam.

5. The absorbent article of claim 1, wherein the substrate layer material comprises an elastic material.

6. The absorbent composite of claim 1, wherein the superabsorbent-containing entities comprise rectangular tiles.

7. The absorbent composite of claim 1, wherein the superabsorbent-containing entities comprise curved platelets.

8. The absorbent composite of claim 1, wherein the superabsorbent-containing entities are attached to the substrate using an adhesive.

9. The absorbent composite of claim 1, wherein the superabsorbent-containing entities are thermally bonded to the substrate.

10. The absorbent composite of claim 1, wherein the superabsorbent-containing entities are ultrasonically bonded to the substrate.

11. The absorbent composite of claim 1, wherein the superabsorbent-containing entities are stitch-bonded to the substrate.

12. A diaper comprising the absorbent composite of claim 1.

13. Training pants comprising the absorbent composite of claim 1.

14. Absorbent underpants comprising the absorbent composite of claim 1.

15. Swim wear comprising the absorbent composite of claim 1.

16. An adult incontinence product comprising the absorbent composite of claim 1.

17. A feminine hygiene product comprising the absorbent composite of claim 1.

18. A medical absorbent product comprising the absorbent composite of claim 1.

19. An absorbent article, comprising:

a liquid-permeable body-side liner;

a substantially liquid-impermeable outer cover; and an absorbent composite between the body-side liner and the outer cover, wherein the absorbent composite comprises a plurality of discrete superabsorbent-containing entities arranged on a substrate having a central region and two end regions; the substrate having a longitudinal direction and a lateral direction;

each discrete superabsorbent-containing entity being attached only to the substrate at an attachment point which leaves most of the entity free of binding so that adjacent entities may expand and slide relative to each other;

the superabsorbent-containing entities in the central region being oriented in the longitudinal direction of the substrate;

the superabsorbent-containing entities in the two end regions being oriented in the lateral direction of the substrate.

20. An absorbent composite, comprising a substrate layer material; and a plurality of discrete superabsorbent-containing entities attached to the substrate, each discrete superabsorbent-containing entity being attached only to the substrate at an attachment point which leaves most of the entity free of binding so that adjacent entities may expand and slide relative to each other;

the superabsorbent-containing entities being imbricated so that a leading edge of at least some of the superabsorbent-containing entities overlaps a trailing edge of an adjacent superabsorbent-containing entity, and wherein the plurality of discrete superabsorbent-containing entities are comprised of a structure wherein the substrate is folded in corrugated fashion to yield pockets which are filled with a superabsorbent material.

* * * * *